United States Patent [19]

Almogy

[11] Patent Number: 6,122,046
[45] Date of Patent: Sep. 19, 2000

[54] DUAL RESOLUTION COMBINED LASER SPOT SCANNING AND AREA IMAGING INSPECTION

[75] Inventor: Gilad Almogy, Givatayim, Israel

[73] Assignee: Applied Materials, Inc., Santa Clara, Calif.

[21] Appl. No.: 09/165,992

[22] Filed: Oct. 2, 1998

[51] Int. Cl.⁷ .................................................. G01N 21/88

[52] U.S. Cl. ...................................... 356/237.2; 356/371

[58] Field of Search .............................. 356/371, 237.2, 356/237.3, 237.4, 239.7, 239.8

[56] References Cited

U.S. PATENT DOCUMENTS

| | | | |
|---|---|---|---|
| 4,290,698 | 9/1981 | Milana | 356/371 |
| 4,465,371 | 8/1984 | Pernick | 356/237.2 |
| 4,731,855 | 3/1988 | Suda et al. | 382/8 |
| 4,740,708 | 4/1988 | Batchelder | 356/237.3 |
| 5,105,092 | 4/1992 | Natsubori et al. | 356/237.2 |
| 5,125,741 | 6/1992 | Okada et al. | 356/237.2 |
| 5,572,598 | 11/1996 | Wihl et al. | 382/144 |
| 5,737,085 | 4/1998 | Zollars et al. | 356/237.2 |
| 5,805,278 | 9/1998 | Danko | 356/237 |

FOREIGN PATENT DOCUMENTS

96/39619 12/1996 WIPO ............................ G01N 21/00

OTHER PUBLICATIONS

Joseph W. Goodman, *Introduction to Fourier Optics* 2nd edition, McGraw–Hill (1996), chapter 5.

G. Dickerson and R. Wallace, "In–line Wafer Inspection Using 100 Megapixel Per Second Digital Image Processing Technology," *SPIE vol. 1464 Integrated Circuit Metrology, Inspection, and Process Control*, (1992), pp. 584–595.

David Alumot et al., "Dual Sensor Technology for High–Speed Detection of 0.1 Micron Defects," *Proceedings of the SPIE, vol. 1926, Integrated Circuit Metrology, Inspection, and Process Control VII*, (1993), pp. 1–12.

*Primary Examiner*—Richard A. Rosenberger
*Attorney, Agent, or Firm*—Sughrue, Mion, Zinn, Macpeak & Seas, PLLC

[57] ABSTRACT

An optical inspection system for inspecting a substrate includes a light detector, a light source, a deflection system, an objective lens and an optical system. The light source produces an illuminating beam directed along a path to the substrate. The deflection system scans the illuminating beam on a scan line of the substrate. The objective lens focuses the illuminating beam on the substrate and collects light reflected therefrom. The collected beam is angularly wider than the illuminating beam. The optical system directs the collected light beam along a path at least partially different than the path of the illuminating beam and focuses the collected beam on the light detector. In one embodiment, the system additionally includes at least one dark field detector for collecting light deflected from the substrate.

18 Claims, 7 Drawing Sheets

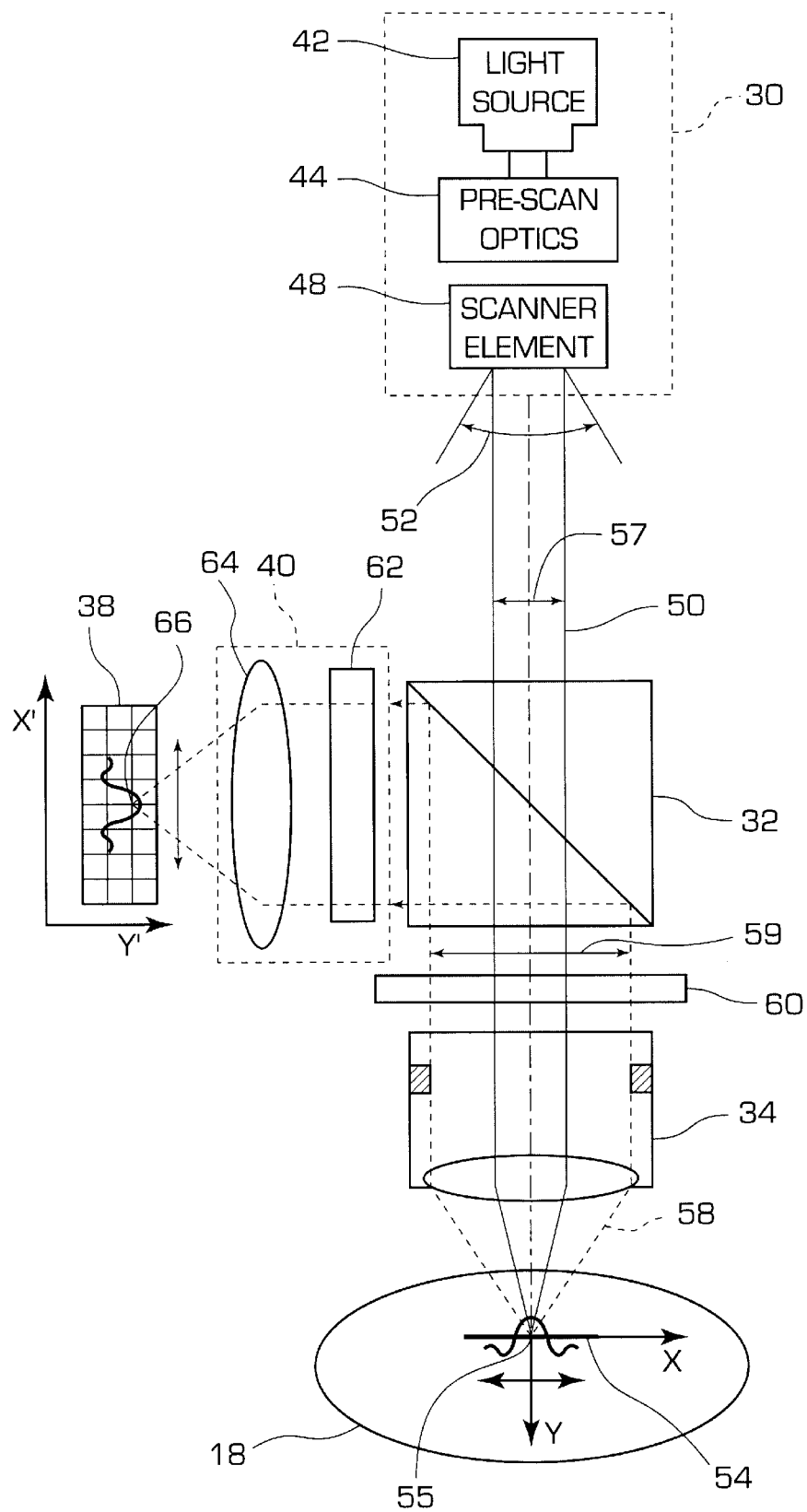

DUAL RESOLUTION COMBINED LASER SPOT SCANNING AND AREA IMAGING INSPECTION

FIELD OF THE INVENTION

The present invention relates generally to systems and methods for detecting irregularities on a substrate and more particularly to systems and methods for detecting irregularities on the surface of silicon wafers or photomasks.

BACKGROUND OF THE INVENTION

Systems which collect optical images of a given substrate can be divided into two categories depending upon the method by which they obtain an image of a given area: area imaging systems and scanning systems. In the former, a whole area of the substrate is illuminated at once and imaging optics are used to project an image of that area or a part of it upon a detector array, typically a CCD camera. Classical optical microscopy works in such a fashion. In another version of imaging systems, a spot, rather than an area, is illuminated and scanned upon the substrate, and the transmitted or reflected light is measured by one or more detectors either directly or after passing through collection optics. In those cases, the illuminating beam may be scanned across the surface in both directions or in just one direction with mechanical motion of the substrate with respect to the beam used to obtain the two dimensional area image.

FIG. 1 exemplifies an area imaging system. It includes a light source 10 which illuminates the object to be inspected (in FIG. 1 the illumination is done via a beam splitter 12 and objective lens 14). The objective lens 14 collects the light reflected from the object and provides an image of the inspected object upon the detector array 16. In contrast, FIG. 2. exemplifies a scanning system. In FIG. 2, a light source 20 generates a light beam 26 which is scanned across the inspected area, 18, using a scanning mechanism 22. The scanning mechanism provides linear scanning, 28, in one direction, while the object is mechanically moved in the perpendicular direction, thereby scanning a two-dimensional area of the object 18. Detectors 24A and 24B are used to detect light reflected from the object.

The resolution characteristics of imaging systems is defined by the point spread function - the form in which a system will image a mathematically ideal spot. An explanation of this phenomenon can be found in Joseph W. Goodman, *Introduction to Fourier Optics,* 2nd edition, McGraw-Hill, 1996, chapter 5. For ideal, diffraction limited, collection optics and a sufficiently dense detector array the system's point spread function is set by the collection optics, typically by the objective lens 14. Its width is proportional to the wavelength and inversely proportional to the imaging optics' numerical aperture.

Unlike the system's point spread function, the system's modulation transfer function (MTF), which is a measure of its spatial frequency response, depends on the illumination optics as well. (See, Joseph W. Goodman, *Introduction to Fourier Optics,* 2nd edition, McGraw-Hill, 1996, chapter 6.) When the illumination across the surface has a definite phase relationship, the system is termed perfectly coherent. When the illumination is incident from multiple directions, the definite phase relationship is lost and the system becomes either partially coherent or incoherent. When the sine of the illumination angle or its numerical aperture is equal to the imaging numerical aperture or greater, the system is termed totally incoherent. The cutoff frequency of the system's MTF is defined as the spatial frequency above which the system has zero response. For coherent systems, the MTF cutoff is half that of incoherent ones. Furthermore, when sharp features such as edges are imaged by coherent systems, the images display oscillations termed "ringing".

In scanning systems, on the other hand, light is focused upon a small spot of the substrate to be imaged and is moved across it in one or two dimensions. Some of the light that is reflected from the spot is collected upon at least one detector which is sequentially sampled. The detector's output along with the knowledge of the spot's location at any given time is used to reconstruct an image of the area scanned. The detector may capture any light scattered into a given spatial angle or may have limiting apertures which limit incoming light to that reflected from the focal spot of the scanning illumination, such as in confocal laser microscopy.

A key disadvantage of scanning systems is their serial, rather than parallel nature, i.e., it takes longer to construct an image using a scanning system. According to the Nyquist theorem, sampling the detectors at a rate that is more than twice the cutoff frequency does not increase the system's frequency response. Therefore meaningful pixels can only be generated at a rate proportional to the time in which the scanning spot can transverse itself. This rate is set by the scanning mechanism (typically an acoustic-optical deflector (AOD), a rotating polygon, or resonant mirrors) and is typically limited to several tens of Mega-pixels per second. Area imaging systems do not suffer from this limitation as a large area could be simultaneously imaged upon a detector array and read out in parallel through more than one output or tap.

A key advantage of scanning systems over area imaging systems is the ability to use laser sources which have both a high brightness and a potentially narrow spectral emission range. The latter is particularly important for UV optical systems where it is difficult to correct for spectral aberrations, When lasers are used in area imaging systems, they lead to half the MTF cutoff frequency of incoherent illumination as well as coherent phenomena such as ringing of edges and speckles. Schemes exist for destroying the coherence of the laser sources but they inevitably add to the system's complexity as well as lead to a loss of optical power.

Besides the division between area illumination-based systems and laser-spot scanning-based systems, imaging systems are also divided by the direction of the illumination with respect to the collection optics. If the illumination impinges upon the substrate from a direction such that the specularly transmitted or reflected light is collected by the imaging optics, the system is termed "bright field"(BF). The imaging system depicted in FIG. 1 is a bright field system, i.e., since the wafer 18 is illuminated perpendicularly, it reflects the light also perpendicularly—in the direction of the detector array 16. If, on the other hand, the illumination arrived from a direction which is outside the collection angle of the imaging optics, the system is termed "dark field"(DF). The scanning system depicted in FIG. 2 is a dark field system, i.e., the light beam 26 impinges upon the wafer perpendicularly and hence the light would normally be reflected perpendicularly—not in the direction of detectors 24A and 24B. Only light reflected from irregularities on the wafer 18 will be reflected towards detectors 24A and 24B. Dark field imaging is used to enhance edge phenomena by collecting only the diffusively reflected light. When used for optical inspection, dark-field laser scanning systems (such as the Orbot WF-731 available from Applied Materials of Santa Clara, Calif.) greatly improve the signal to noise ratio for small, three dimensional objects in a mostly flat background. Furthermore, using several detectors located in different angles within the dark field (such as in the WF-731) increases the chance of defect capture and reduces the chance for false alarms. As a result, it is possible to detect defects that are significantly smaller than the system's spatial resolution and hence it is possible to scan the substrate using relatively large pixels and thus achieve a very high system throughput.

Other inspection systems, such as the one described in U.S. Pat. No. 5,805,278 by J. Danko and the KLA-2230, available from KLA of San Jose, Calif., use dark-field illumination and area imaging optics to enjoy some of the same advantages. Yet other systems, such as the Orbot WF-736, also available from Applied Materials, use laser scanning and a combination of dark-field and bright field detection. A limitation on such systems is that the resolution of the bright-field channel is equal to that of the dark-field ones although the signal to noise ratio for the bright-field channel is inherently inferior. It therefore may be difficult to detect defects that are small and flat.

Another system of interest is described in PCT application WO 96/39619. That system includes an area imaging system which utilizes two light sources of different wavelengths to simultaneously collect both a dark-field and a bright field image. This system has the disadvantage of requiring what are essentially two separate imaging paths including two illumination sources, two detector arrays and alignment between these two channels.

SUMMARY OF THE INVENTION

It is an object of the present invention to combine both the advantages of laser-scanning dark-field imaging systems and of area illumination bright-field imaging systems. In accordance with a preferred embodiment an area of a substrate is scanned in one direction with a laser spot using an illumination system with a given numerical aperture ($NA_{ill}$). Scanning in the other direction is achieved via mechanical motion of the substrate with respect to the scan line. The light around the direction of either the specular reflection and/or the specular transmission is collected via an objective lens with a numerical aperture ($NA_{col}$) that is larger than that of the illumination path ($NA_{ill}$). At the same time, light which is reflected outside the direction of the specular reflection may be collected with one or more dark field detectors whose resolution is determined by that of the scanning spot and hence by the illumination optics. Therefore, with one laser illumination source a high resolution bright-field image is obtained simultaneously with one or more lower resolution dark-field images where the bright-field's resolution enhancement depends on the ratio of the collection numerical aperture to the illumination numerical apertures ($NA_{col}/NA_{ill}$).

The bright-field reflection or transmission is imaged upon a detector array with the proper optics as to obtain an image with a spatial resolution or point spread function which is determined by the collection optics' numerical aperture and is finer than that of the illumination spot. These optics are designed with the proper magnification of the scan line's image upon the detector array so that the array's elements are small enough in comparison with the point spread function and do not limit the resolution. The number of effective elements in the array along the laser scan direction is therefore larger than the number of pixels in a dark-field image by a factor on the order of the resolution ratios (coherence and other imaging considerations may dictate a different ratio between the point spread function and pixel sizes for the bright-field and the dark-field). The bright-field imaging array may also have more than one pixel per dark-field pixel in the direction perpendicular to the laser s scan (i.e. that of the mechanical motion). Again the number of effective elements is determined by the resolution enhancement ratio and by the required ratio of the point spread function to the pixel size.

In accordance with a preferred embodiment, the resolution of either the illumination optics or the collection optics need not be identical in the laser scanning and mechanical scanning direction. The illumination optics may have low resolution in one axis only, for which the collection optics would only have resolution enhancement. Alternatively the illumination optics may have equal resolution in both axes and the collection optics may improve the resolution along one axis only.

In this embodiment, only the data-rate of the dark-field images is limited by the scanning mechanism, i.e., by the time it takes the optical spot to transverse itself. Since the bright-field image has a higher resolution which is determined mainly by the collection optics, its data-rate limit is not set by the scanning mechanism. Rather, the limit on the bright-field data-rate is the dark-field data rate multiplied by the square of the resolution enhancement obtained. It is thus possible to scan a substrate at a high throughput with relatively large dark-field pixels, whose data-rate is set by the scanning mechanism, simultaneously with collecting a high-resolution bright-field image which uses the same illumination spot but whose data-rate is unlimited by it.

Another advantage of this embodiment is the possibility of using a laser source, and since only a single spot is illuminate at any given instance, not suffering from the full effects of coherent illumination.

There is therefore provided, in accordance with a preferred embodiment of the present invention, an optical system which includes both bright-field and dark-field inspection using a single, scanning illumination system. The optical system includes a light detector, a light source, a deflection system, an objective lens and an optical system. The light source produces an illuminating beam directed along a path to the substrate. The deflection system scans the illuminating beam on a scan line of the substrate. The objective lens focuses the illuminating beam on the substrate and collects light reflected therefrom. The collected beam is angularly wider than the illuminating beam. The optical system directs the collected light beam along a path at least partially different than the path of the illuminating beam and focuses the collected beam on the light detector.

In one embodiment, the system additionally includes at least one dark field detector for collecting light deflected from the substrate. In accordance with a preferred embodiment of the present invention, the system also includes a processing unit for generally simultaneously processing the output of the dark field detector and the light detector.

Moreover, in accordance with a preferred embodiment of the present invention, the output of the dark field detector and the light detector are of different resolution and pixel sizes.

Additionally, in accordance with a preferred embodiment of the present invention, the optical system also includes a quarter-wave plate for polarizing the collected beam in a direction different from that of the illuminating beam and a polarizing beam-splitter for directing the illuminating beam in the direction of the substrate and for redirecting the collected beam towards the light detector.

Further, in accordance with a preferred embodiment of the present invention, the light detector is an array detector, such as a charge coupled device (CCD) array or a time delay and integration (TDI) CCD array. In one embodiment, the array reads out one portion of the array while a second portion of the array is being illuminated. In another embodiment, the array includes a plurality of pixels along a principal dimension corresponding to the scan line and substantially less pixels along a dimension orthogonal to the principal dimension.

Still further, in accordance with a preferred embodiment of the present invention, the optical system includes a lens whose magnification is higher in the principal dimension than in the orthogonal dimension.

Finally, in accordance with a preferred embodiment of the present invention, the numerical aperture of the objective lens is larger than the numerical aperture of the deflection system.

BRIEF DESCRIPTION OF THE DRAWINGS

The present invention will be understood and appreciated more fully from the following detailed description taken in conjunction with the appended drawings in which:

FIGS. 5A, 5B, 5C, 6A, 6B and 6C are graphical illustrations of the output of the present invention for the dark-field and bright-field systems, respectively, wherein FIGS. 5A and 6A illustrate the scattering-profiles, FIGS. 5B and 6B illustrate the point spread functions and FIGS. 5C and 6C illustrate the output signals of the two systems;

FIG. 7 is a schematic illustration of a bright-field inspection system using scanning illumination, constructed and operative in accordance with an alternative preferred embodiment of the present invention.

DETAILED DESCRIPTION OF THE PRESENT INVENTION

Figure 1:
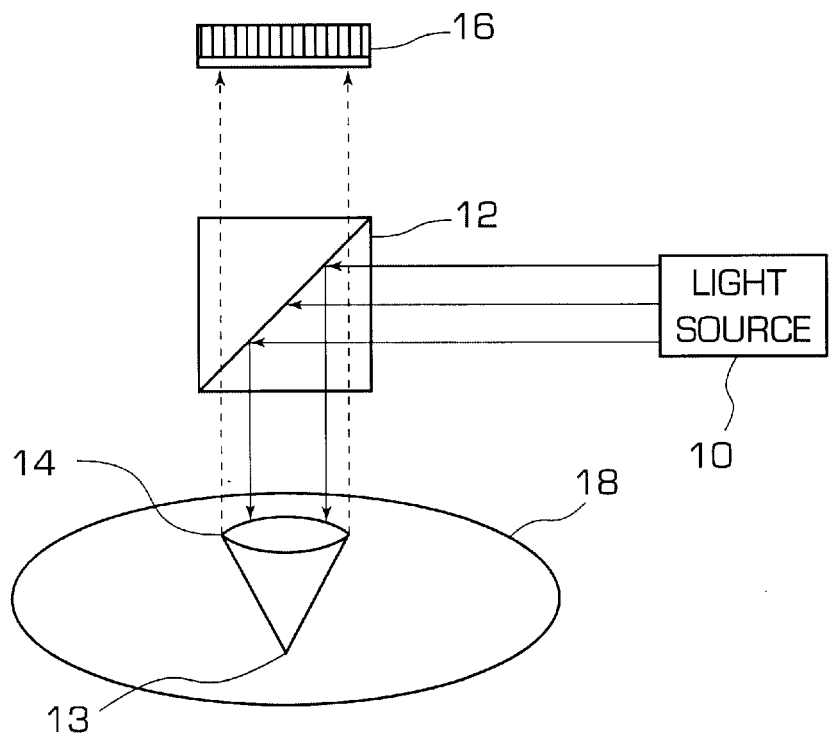
FIG. 1 is a schematic illustration of a prior art bright-field imaging system.
Figure 2:
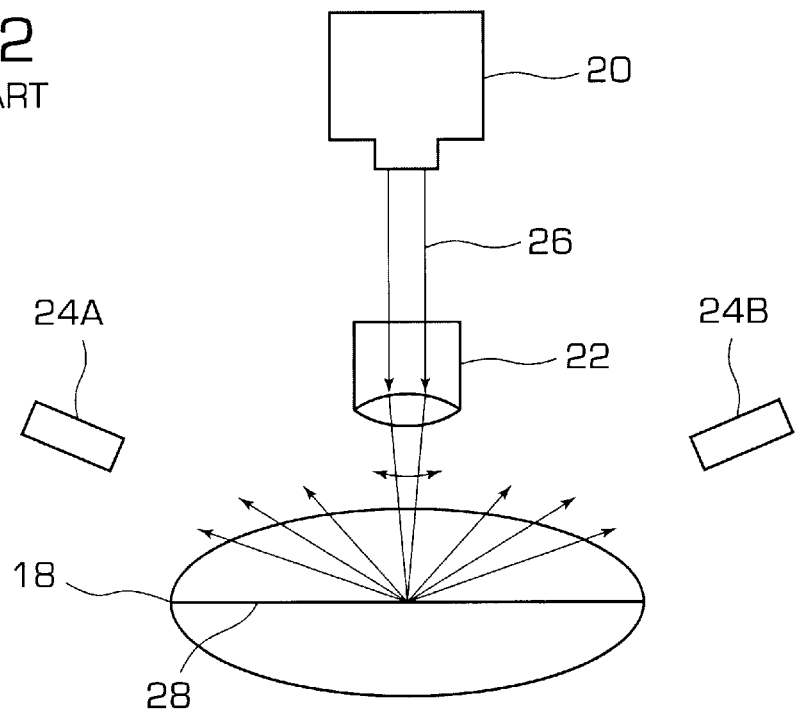
FIG. 2 is a schematic illustration of a prior art dark-field inspection system.
Figure 3A:
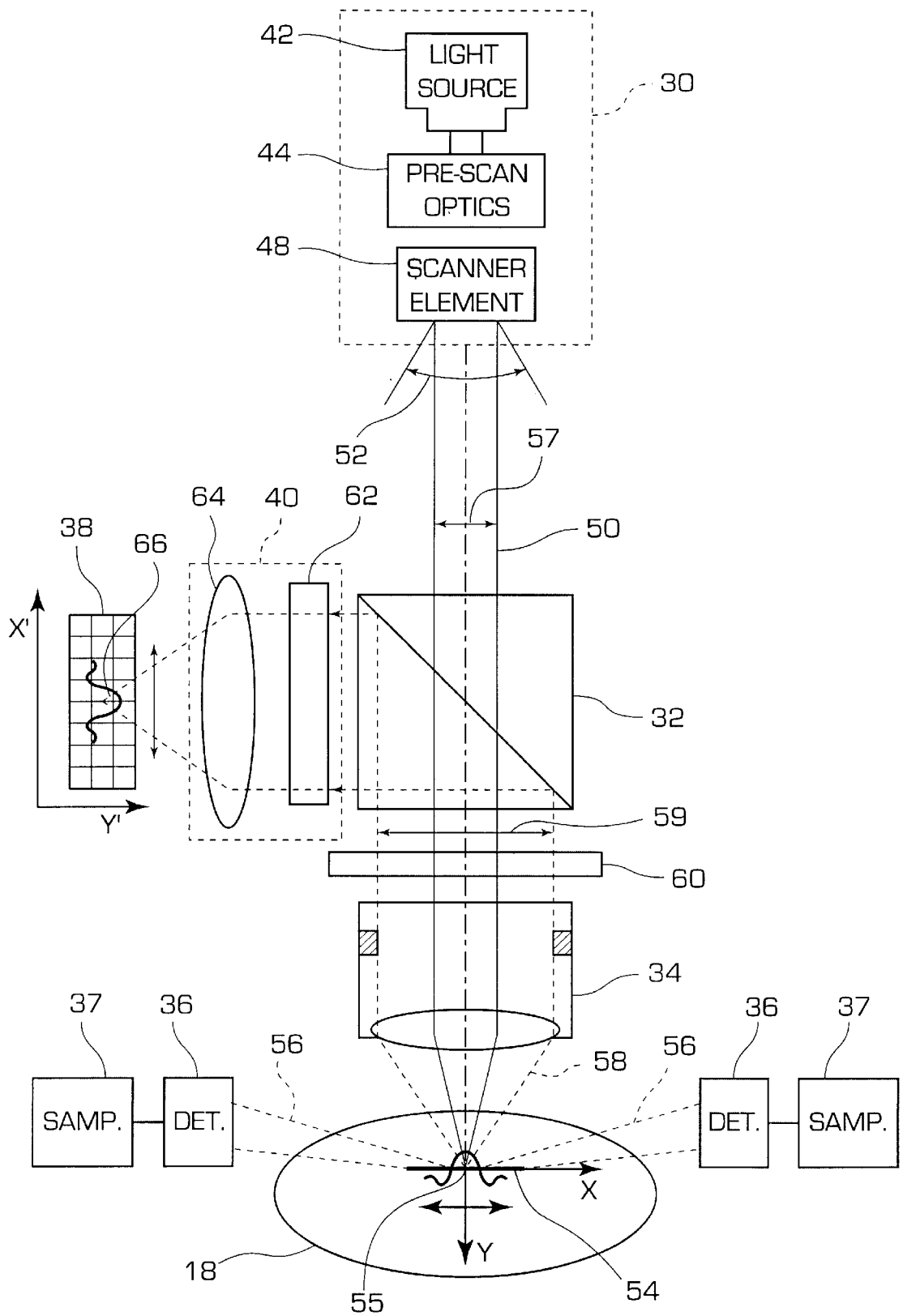
FIG. 3A is a schematic illustration of a combined bright- and dark-field inspection system, constructed and operative in accordance with a preferred embodiment of the present invention.
Figure 3B:
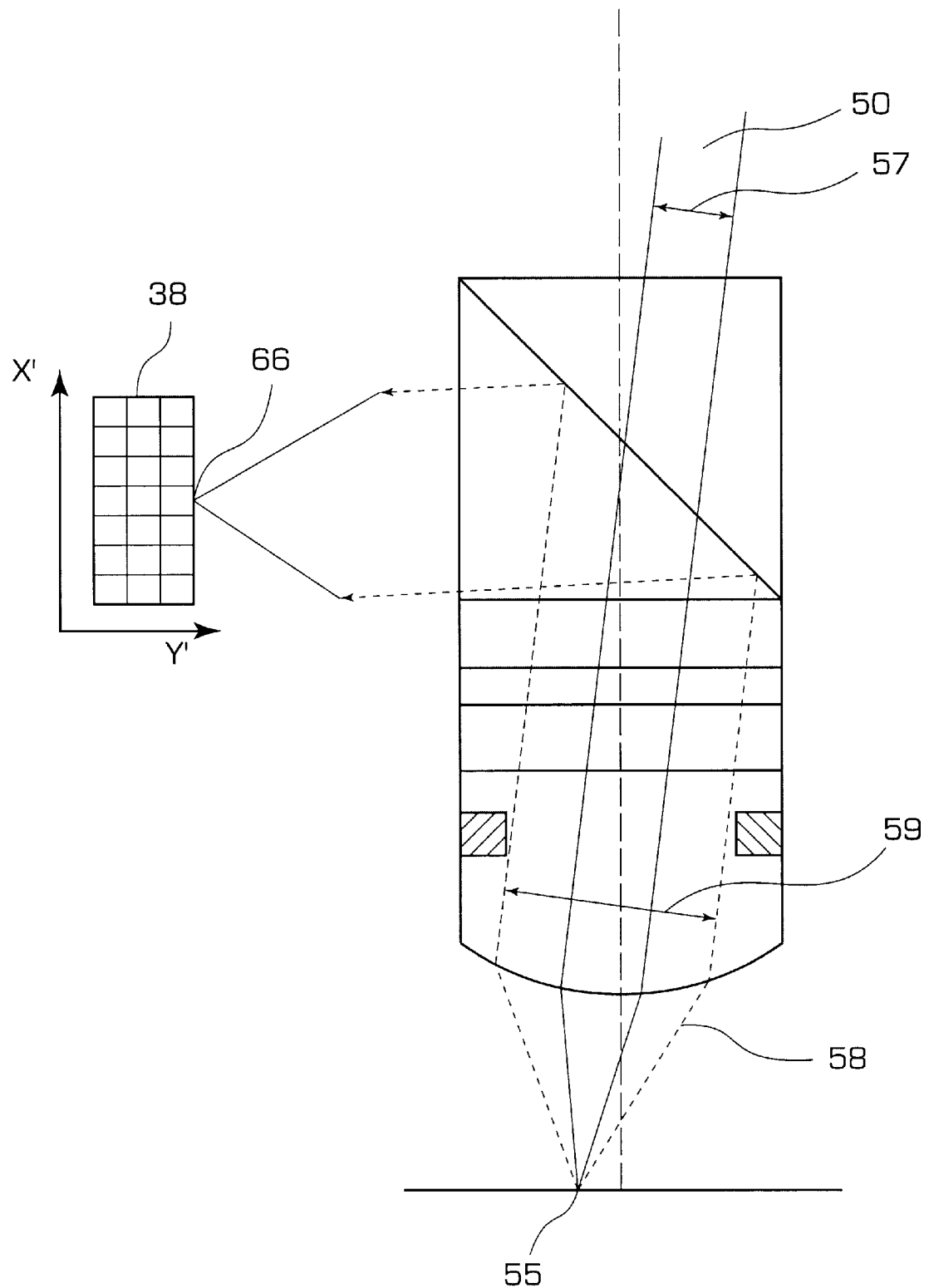
FIG. 3B is a schematic illustration of the scanning operation, useful in understanding the operation of the system of FIG. 3A.

Reference is now made to FIGS. 3A and 3B which illustrate an inspection device of the present invention providing both bright field and dark field techniques with a single set of illumination optics in two different states.

The inspection device typically comprises a scanning illumination system 30, a beam splitter 32, an objective 34, dark field detectors 36, data samplers 37, a bright field detector 38 and an optical system 40 forming part of the bright field collection optics. The scanning illumination system 30 comprises a light source 42, pre-scan optics 44, such as a quarter-wave plate, and a scanning element 48 such as an.

As indicated by arrow 52, the scanning illumination system 30 scans an illuminating light beam 50 through beam splitter 32. FIG. 3A shows the light beam 50 in a centered position while FIG. 3B shows the light beam 50 at an extreme position. Objective 34 then converts the angular scan into a focused linear scan along a scan line 54 on substrate 18. The deflected light beams 56 are detected by the dark field detectors 36, such as photomultipliers, whose output is sampled by data samplers 37 as in the prior art, wherein the sampling rate is a function of the scanning rate.

For bright field imaging, objective 34 collects light 58 reflected from spot 55 and passes it to beam splitter 32 via a second polarizing element 60, such as a quarter-wave plate, which changes the polarization of light beam 58 from that of incoming beam 50. Accordingly, beam splitter 32 is a polarizing beam splitter which deflects the differently polarized, reflected light beam 58 away from the illumination path and towards bright field detector 38 via optical system 40.

Typically, optical system 40 is any system which processes the reflected light beam 58 and which focuses it onto bright field detector 38. For example, optical system 40 can comprise a variable aperture 62 and a focusing objective 64. The variable aperture 62 spatially filters the reflected light. Objective 64 focuses the filtered and reflected light onto bright field detector 38. which is typically an array of photoelements, such as are found in charge coupled devices (CCDs). As the illumination spot 55 scans across scan line 54. the reflected spot, labeled 66, scans along the bright field detector 38.

It will be appreciated that the angular distribution of the light reflected from a focused spot 55 on the substrate 18 depends on the surface qualities of the substrate 18. For a perfectly flat surface containing no spatial information, all of the light will be specularly reflected back to objective 34. Substrates with a very high spatial frequency (i.e. small features) and those with three-dimensional features deflect a significant amount of light at low angles. This deflected light is detected by the dark-field detectors 36.

The focused spot 55 has a minimal size which is determined by the numerical aperture $NA_{ill}$, labeled with arrow 57, of the illumination optics. Numerical aperture $NA_{ill}$, which is relatively narrow, is defined by the illumination optics. It will be appreciated that the ratio of the numerical aperture $NA_{ill}$, to the scan angle, and hence the ratio of the scan line length to the spot size, is typically limited by the scanning element 48.

Applicant has realized that the resolution of a bright-field image depends mainly on the collection numerical aperture $NA_{col}$, labeled with arrow 59. In accordance with a preferred embodiment of the present invention, the collection numerical aperture $NA_{col}$ is larger than the illumination numerical aperture $NA_{ill}$, This is achieved by selecting an objective 34 whose numerical aperture NA is larger than that defined by the illumination optics. Since the bright-field collection optical path does not include the scanning element 48, the collection numerical aperture $NA_{col}$ and the bright-field collection resolution are independent of the limitations of the scanning element 48. Furthermore, due to the high speed scanning of the small spot, illumination beam 50 has the same effect as partially coherent illumination which is often used in standard bright-field microscopy.

The increased aperture bright-field image collects higher spatial frequencies and has better spatial resolution than would either imaging collection through the illumination aperture only or a non-imaging collection of the bright field (such as with photomultipliers).

It will be appreciated that the pixel size $P_{DF}$ for the dark-field collection channel is a function of the velocity of the scanned spot 55 and of the sampling period of the samplers 37. The effective resolution, however, is limited by the illumination numerical aperture $NA_{ill}$. The pixel size $P_{BF}$ for the bright-field collection, on the other hand, is determined by the size of each photoelement of the bright-field detector 38. The effective resolution for the bright-field is determined mainly by the collection numerical aperture $NA_{col}$.

To obtain a two dimensional image, the laser spot 55 is typically scanned in one direction (the X direction marked in FIGS. 3A and 3B) while the substrate 18 is mechanically moved in a perpendicular direction (not shown). To obtain square pixels, the mechanical velocity is chosen so that the substrate 18 moves by one pixel in the Y direction in the time it takes to perform a full scan in the X direction. During the scan, the reflected spot 66 will scan across the bright-field detector array 38.

The dark field pixel $P_{DF}$ is defined by the sampling period $(t_{smp})$ and the scan velocity V of the spot 55 on the object plane as follows:

$$P_{DF}=V*t_{smp}$$

The proportion between the size S of the spot 55 and the size $P_{DF}$ of the dark field pixel is termed the sampling rate SR, where $SR=S/P_{DF}$, and is chosen from considerations of sampling theory, the modulation transfer function of the system and rate limitations on the image processing (not shown). The magnification of the bright-field collection path is chosen so that the required size $P_{BF}$ of the bright-field pixel is magnified to the size of one photoelement of the bright-field detector 38.

Figure 4A:
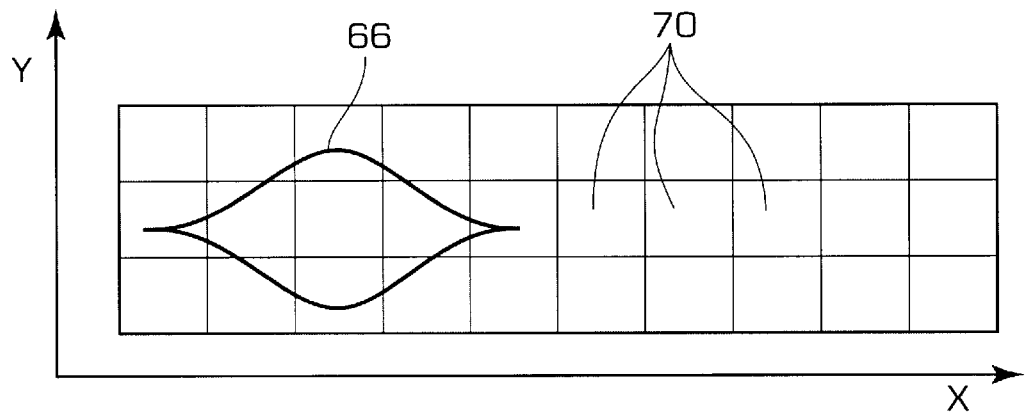
FIGS. 4A and 4B are schematic illustration of charge coupled detectors, useful in the system of the present invention.

FIG. 4A, to which reference is now made, is a schematic illustration of the bright-field image generation with a multi-line detector 38. The embodiment of FIG. 4A assumes a 3:1 ratio R between the sizes of the dark and bright field pixels, where R is defined as $P_{DF}/P_{BF}$. The bright-field detector 38 is thus an array of R rows, each having RN pixels, where N is the number of pixels in the dark-field scanline.

Figure 4B:
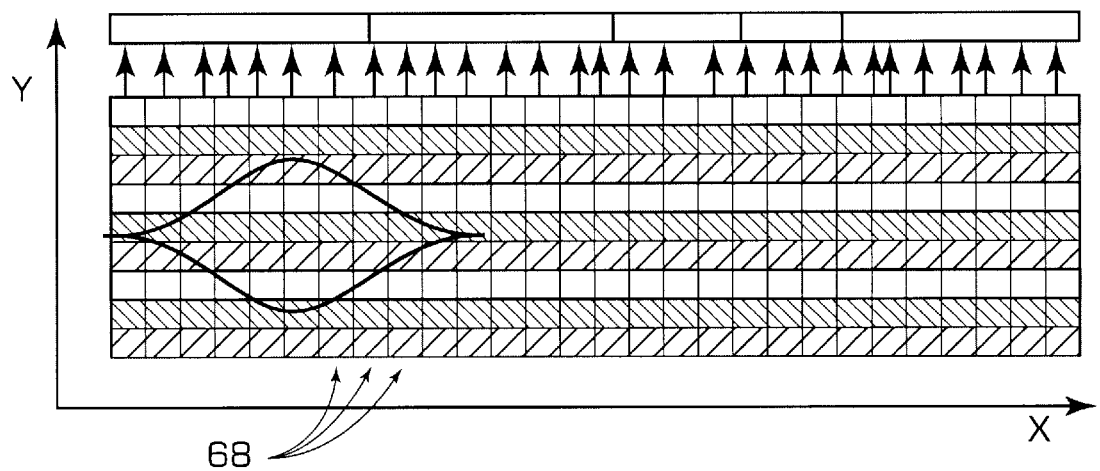

Each pixel, labeled 70, of the bright-field detector 38 is read once every scan period. Thus, as the spot 66 travels along the detector, as shown in FIG. 4 the charge at each pixel is integrated until the reading period. The integration provides an average uniform illumination in the scan direction. This uniform illumination reduces the affects of speckle phenomena which occur due to the loss of coherence between spots along the scan line 54.

In the Y direction, however, only a portion of the spot 66 illuminates each pixel. This non-uniformity is typically corrected by an image processing unit (not shown) or through the use of a commercially available time delay and integration (TDI) detector, shown in FIG. 4B, to which reference is now briefly made.

Alternatively, the detector 38 can be a multi-tap detector which read out different parts of the array 68 separately. In this embodiment and due to the scanning illumination of the present invention, some columns can be readout while other columns are being illuminated. This enables collection of all the light without a dedicated read-out time.

Other types of array detectors are possible and are incorporated into the present invention.

Figure 5A:
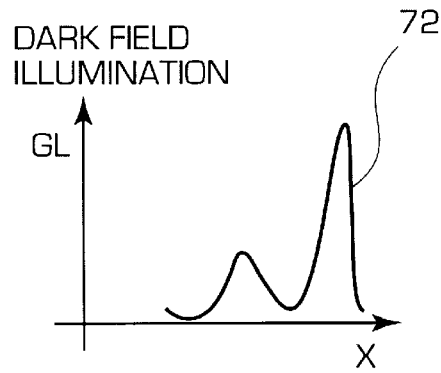
Figure 6A:
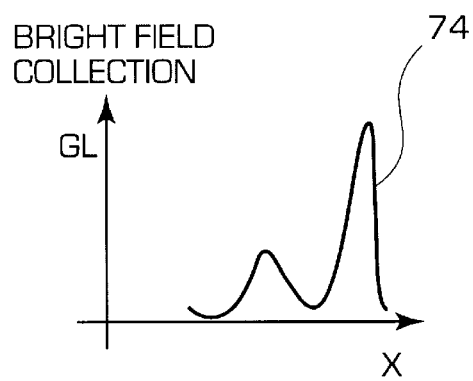
Figure 5B:
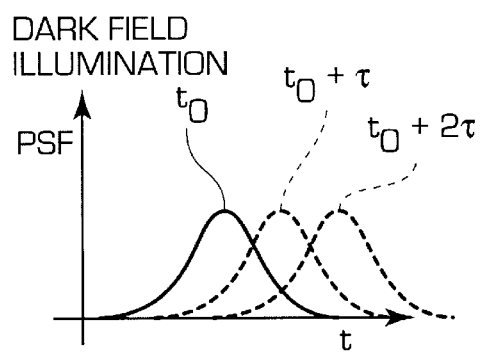
Figure 6B:
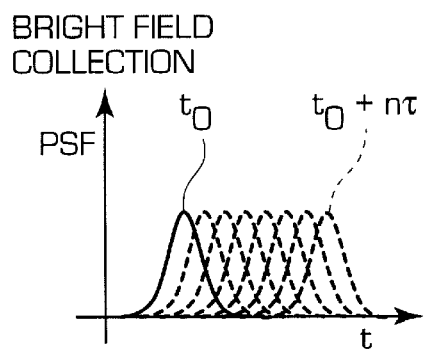
Figure 5C:
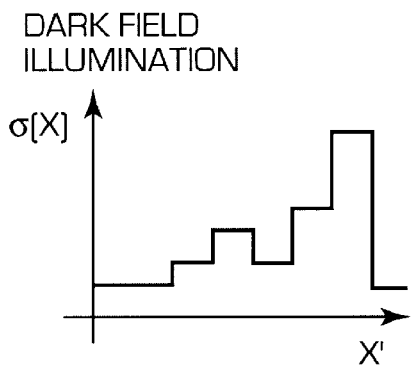
Figure 6C:
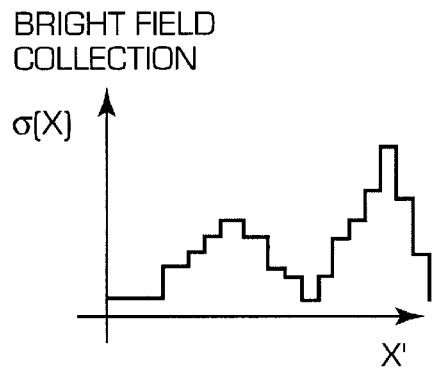

Reference is now made to FIGS. 5 and 6 which illustrate the output of the present invention for the dark-field and bright-field systems, respectively. FIGS. 5A and 6A illustrate the scattering-profiles, FIGS. 5B and 6B illustrate the point spread functions and FIGS. 5C and 6C illustrate the output signals of the two systems.

The scattering profiles 72 and 74 are graphs of intensity vs. distance along the scan line and may or may not be similar to each other for the two systems. For simplicity, the two graphs are shown identical.

FIG. 5B illustrates the point-spread function of the dark-field spot at sequential sampling times $t_i$ while FIG. 6B shows the same for the bright-field image. The sampling for the dark-field is less frequent than for the bright-field because the dark-field has a larger point spread function.

According to sampling theory, when the sampling rate is above twice the limit of the spatial frequencies of the illumination spot, all the available image information may be retrieved from the digitized image. The output of the dark-field system (FIG. 5C) is a quantized version of the signals of FIG. 5B; similarly for FIG. 6C. However, FIG. 6C (the output of the bright-field system) is of higher resolution. This is due to the higher, collection numerical aperture $NA_{col}$ which allows for higher frequencies and collecting more information than available with the lower, illumination numerical aperture $NA_{ill}$ of the bright-field scanning system. Thus, the bright-field system can be utilized to view that seen in the dark-field system at higher resolution.

It will be appreciated that the two collection systems produce data at he same time. This data can be combined or used individually, as desired.

Reference is now briefly made to FIG. 7 which illustrates an alternative embodiment of the present invention for bright-field imaging only. FIG. 7 is similar to FIG. 3A and thus, similar reference numerals refer to similar elements.

In this embodiment, there are no dark-field detectors 36 or samplers 37. The remaining elements are the same. Thus, the illumination beam 50 is scanned across the substrate 18, the reflected beam 58 has a larger numerical aperture than that of the illumination beam 50 and the reflected beam 58 is polarized thereby to be deflected by the beam splitter 32 onto the array detector 38.

As discussed hereinabove, the scanned light beam provides partially coherent illumination to the bright-field detector 38.

It will be appreciated that the optical elements of the present invention can either be spherical or cylindrical, or a combination of both. For cylindrical illumination, the numerical aperture will be large in one axis but small in the axis orthogonal to the large axis. If spherical collection is used, the numerical aperture will be large in both axes. Alternatively, spherical illumination can be utilized with cylindrical collection.

Figure 8:
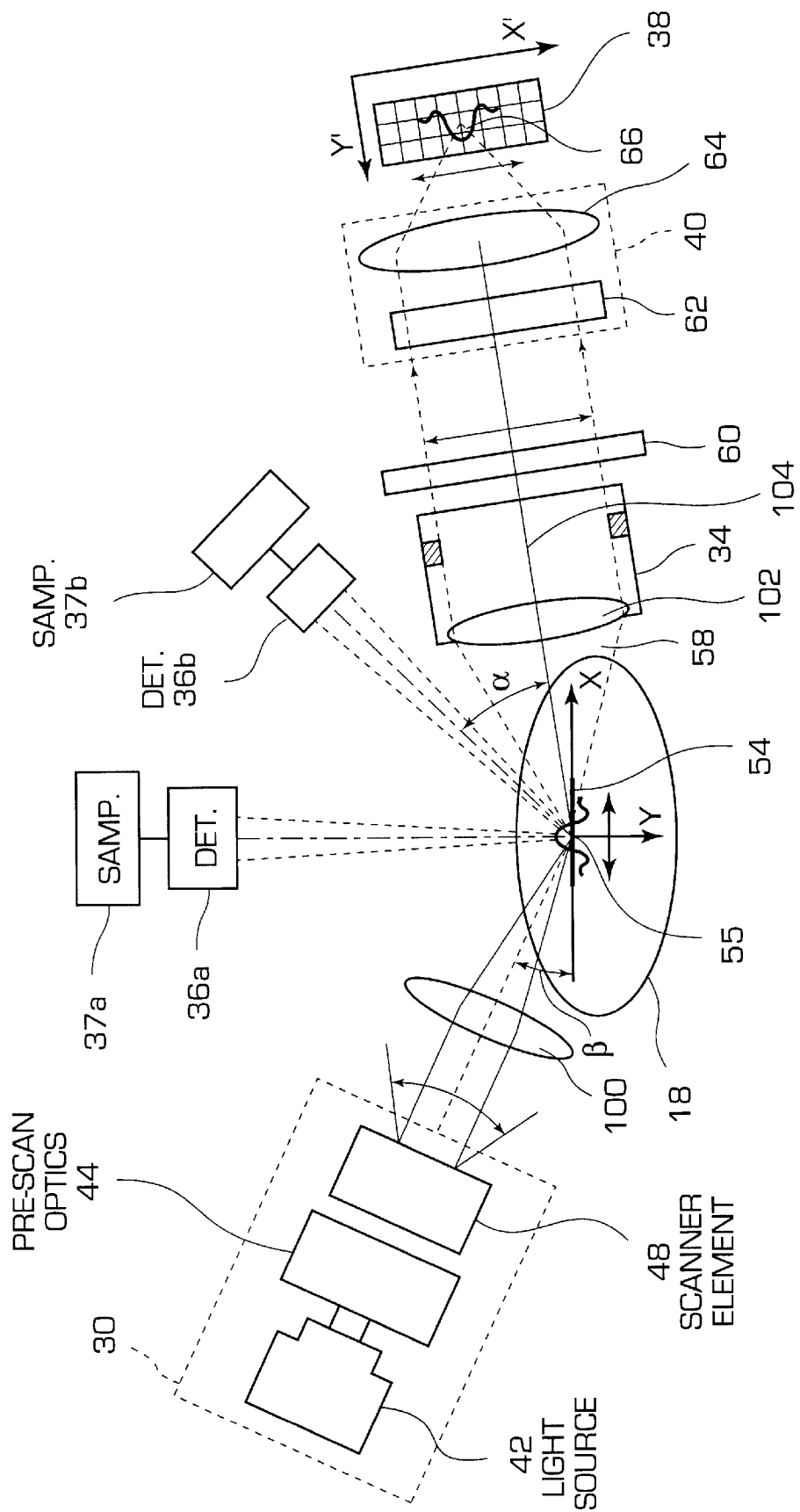
FIG. 8 is a schematic illustration of an alternative combined bright- and dark-field inspection system, constructed and operative in accordance with a preferred embodiment of the present invention.

Reference is now made to FIG. 8 which illustrates an alternative embodiment of the present invention. In this embodiment, the scanning illumination is at an acute angle β to the surface rather than being normal to the surface as in the previous embodiments. Similar elements carry similar reference numerals.

In this embodiment, the collection optics (to the right of the surface 18) are separate from the scanning optics (to the left of the surface 18). Accordingly, there is a scanning objective 100 which is separate from a collection objective 102 and, there is no beam splitter. The numerical aperture $NA_{ill}$ of scanning objective 100 is smaller than the numerical aperture $NA_{col}$ of collection objective 102.

The dark field collection can either be from above, as shown with detectors 36a and samplers 37a, or from a spatial angle a from the simple, "Snell's Law" reflection angle of the axis 104 of the reflected beam, as shown with detectors 36b and samplers 37b.

The bright field arrangement depicted in FIG. 8 is advantageous over prior art bright field systems in several respects. First, as noted above, by using a collection objective having a higher numerical aperture, the resolution of the bright field detector can be enhanced. However, regardless of the numerical aperture, the system is also advantageous in that it provides an enhanced topography image. That is, general bright field systems collect light reflected orthogonal to the substrate, thus having low topography resolution. Situating the bright field illumination and collection optics at acute angles to the substrate enhances the topography resolution and thus assists in resolving defects on the substrate.

To appreciate this advantage, one may consider a micro-scratch, such as those usually caused by a chemical-mechanical planerization (CMP) process, on the surface of the substrate. If illuminated from above, as in the prior art, the bottom of the scratch would be illuminated to the same extent as the surroundings, and, depending on their slop, the walls of the scratch may not be illuminated at all or may be illuminated to the same extent. Thus, when collecting the light perpendicularly as in the prior art, the micro-scratch may escape detection. On the other hand, if the bright field illumination is provided in an acute angle per FIG. 8, one wall of the scratch will be illuminated brighter than the other. Thus, when collecting the bright field light at an acute angle, the scratch will appear very good on the detector.

It will be appreciated by persons skilled in the art that the present invention is not limited by what has been particularly shown and described hereinabove. Rather the scope of the invention is defined by the claims that follow:

I claim:

1. A dual resolution inspection system for inspecting a substrate, comprising:
    an illumination system comprising a light source producing an illuminating beam directed along a path to said substrate, and a deflection system for scanning said illuminating beam on at least a scan line of said substrate;
    an illumination objective for focusing said illuminating beam on said substrate and for collecting light reflected therefrom whereby a collected light beam is formed, said collected light beam being angularly wider than said illuminating beam;
    at least one dark field detector for detecting scattered light scattered from said substrate;
    an array light detector; and
    an optical system disposed between said illumination system and said illumination objective for diverting said collected light beam from an optical path connecting said illumination system and said illumination objective and focusing said collected light beam, after said collected light beam passes said illumination objective, onto said array light detector.

2. A device according to claim 1, wherein said optical system comprises a quarter-wave plate for polarizing said collected light beam in a direction different from that of said illuminating beams and a polarizing beam-splitter for directing said illuminating beam in the direction of said substrate and for redirecting said collected light beam towards said array light detector.

3. A device according to claim 1, wherein said array is a charge coupled device (CCD) array or a time delay and integration (TDI) CCD array.

4. A device according to claim 3, further comprising means for reading out one portion of said array while a second portion of said array is being illuminated.

5. A device according to claim 1 wherein said array comprises a plurality of pixels along a principal dimension corresponding to said scan line and substantially less pixels along a dimension orthogonal to said principal dimension.

6. A device according to claim 5, wherein said optical system comprises a collection objective whose magnification is higher in said principal dimension than in said orthogonal dimension.

7. A device according to claim 1 wherein a numerical aperture of said illumination objective is larger than a numerical aperture of said deflection system.

8. A device according to claim 1, further comprising a processing unit for generally simultaneously processing output of said dark field detector and said array light detector.

9. A device according to claim 1, wherein said the output of said dark field detector and said array light detector are of different resolution and pixel sizes.

10. A dual resolution inspection system for inspecting a substrate, comprising:
    an illumination system comprising a light source producing an illuminating beam directed along a path at an angle to said substrate,
    and a deflection system for scanning said illuminating beam on at least a scan line of said substrate;
    an illumination objective for focusing said illuminating beam on said substrate and
    collecting light reflected from said substrate whereby a collected light beam is formed, said collected light beam being angularly wider than said illuminating beam;
    at least one dark field detector for detecting scattered light scattered from said substrate;
    an array light detector; and
    an optical system disposed between said illumination system and said illumination objective for diverting said collected light beam from an optical path connecting said illumination system and said illumination objective and for focusing said collected light beam, after said collected light beam passes said illumination objective, onto said array light detector.

11. A device according to claim 10, wherein a numerical aperture of said illumination objective is larger than a numerical aperture of said deflection system.

12. A dual resolution inspection system for inspecting a substrate, comprising:
    an illumination system comprising a light source producing a light beam, and a deflection system for scanning said light beam on at least a scan line of said substrate;
    illumination optics defining an illumination path for said light beam;
    an illumination objective inserted in said illumination path and having a defined numerical aperture for focusing said light beam on said substrate;
    at lest one dark field detector for detecting scattered light scattered from said substrate;
    a multiple element light sensor
    collection optics defining a collection path for light reflected from said substrate; and
    a collection objective inserted in said collection path and having a defined numerical aperture larger than said numerical aperture of said illumination objective, for focusing said light beam after said light beam, passes said illumination objective, onto said multiple element light sensor.

13. A device according to claim 12, wherein a numerical aperture of said illumination objective is larger than a numerical aperture of said deflection system.

14. A bright-field inspection system for inspecting a substrate, comprising:

an illumination system comprising a laser providing a laser beam, and a deflection system for scanning said laser beam on at least a scan line of said substrate;

illumination optics defining an illumination path for said laser beam and focusing said laser beam on said substrate at an acute incidence angle, said illumination optics having a defined illumination numerical aperture;

collection optics situated to collect light reflected at an acute angle opposite said acute incidence angle and defining a collection path, said collection optics having a defined collection numerical aperture larger than said illumination numerical aperture; and an array light detector situated in said collection path.

15. The bright field inspection system of claim 14, further comprising:

an illumination objective inserted in the illumination path and having a defined numerical aperture; and a collection objective inserted in the collection path and having a defined numerical aperture larger than the numerical aperture of the illumination objective.

16. A device according to claim 15, wherein a numerical aperture of said illumination objective is larger than a numerical aperture of said deflection system.

17. A device according to claim 14, further comprising at least one dark field detector situated to collect light scattered from said substrate.

18. A dual resolution inspection system for inspecting a semiconductor wafer, comprising:

an illumination system comprising a light source for producing an illumination beam at an acute angle to said substrate, and a deflection system for scanning said illumination beam on at least a scan line of said substrate;

an illumination objective for focusing said illumination beam on said substrate and having a defined illumination numerical aperture;

at least one dark field detector for detecting scattered light scattered from said semiconductor wafer, said dark field detector located at a spatial angle from specular reflection of said illumination beam;

a collection objective for collecting light reflected from said substrate whereby a collected light beam is formed, said collection objective having a defined collection numerical aperture larger than said illumination numerical aperture; and an array light detector receiving said collected light beam.

* * * * *